(12) United States Patent
Coates et al.

(10) Patent No.: US 6,344,154 B1
(45) Date of Patent: Feb. 5, 2002

(54) REACTIVE LIQUID CRYSTAL COMPOUNDS

(75) Inventors: David Coates, Wimborne; Simon Greenfield, Poole; Emma Jolliffe, Weymouth; Ian Victor Hassall, Christchurch; Alison May, Wimborne, all of (GB)

(73) Assignee: Merck Patent GmbH, Darmstadt (DE)

(*) Notice: Subject to any disclaimer, the term of this patent is extended or adjusted under 35 U.S.C. 154(b) by 0 days.

(21) Appl. No.: 09/563,903

(22) Filed: May 4, 2000

Related U.S. Application Data (62) Division of application No. 09/117,787, filed as application No. PCT/EP97/00843 on Feb. 21, 1997, now abandoned.

(30) Foreign Application Priority Data

Mar. 19, 1996 (EP) ............................................. 96104330

(51) Int. Cl.$^7$ ........................ C09K 19/30; C09K 19/38; C07C 69/76; C07D 303/12; C08F 20/18; C08G 59/24

(52) U.S. Cl. ............................ 252/299.63; 252/299.67; 428/1.1; 428/1.5; 560/64; 560/95; 549/208; 525/330.3; 526/318.44

(58) Field of Search .................... 252/299.1, 299.67, 252/299.63; 428/1.1, 1.5; 560/64, 85, 95; 525/330.3; 526/318.44; 549/208

(56) References Cited

U.S. PATENT DOCUMENTS

| | | |
|---|---|---|
| 4,130,502 A | 12/1978 | Eidenschink et al. |
| 5,013,477 A | 5/1991 | Buchecker et al. |
| 5,024,850 A | 6/1991 | Broer et al. |
| 5,188,760 A | 2/1993 | Hikmet et al. |
| 5,238,602 A | 8/1993 | Petrzilka et al. |
| 5,332,520 A | 7/1994 | Bach et al. |
| 5,506,704 A | 4/1996 | Broer et al. |
| 5,518,652 A | 5/1996 | Parri et al. |
| 5,560,864 A | 10/1996 | Goulding |
| 5,622,648 A | 4/1997 | Parri et al. |
| 5,709,911 A | 1/1998 | Onishi et al. |
| 5,723,066 A | 3/1998 | Coates et al. |
| 5,863,457 A | 1/1999 | Hasebe et al. |
| 5,989,461 A | * 11/1999 | Coates et al. ............... 252/585 |
| 6,096,241 A | * 8/2000 | Coates et al. ........... 252/299.01 |
| 6,117,920 A | * 9/2000 | Jolliffe et al. ............... 522/170 |

FOREIGN PATENT DOCUMENTS

| | | |
|---|---|---|
| DE | 26 36 684 | 2/1978 |
| DE | 195 04 224 | 8/1995 |
| EP | 168 683 | 1/1986 |
| EP | 261 614 | 3/1988 |
| EP | 315 050 | 5/1989 |
| EP | 331 933 | 9/1989 |
| EP | 397 263 | 11/1990 |
| EP | 451 905 | 10/1991 |
| EP | 606 940 | 7/1994 |
| EP | 659 856 | 6/1995 |
| EP | 659 865 | 6/1995 |
| JP | 08-209127 | * 8/1996 |
| WO | 93 22397 | 11/1993 |

OTHER PUBLICATIONS

English Abstract of JP 08–209127, 1996.*
D. J. Broer et al., *Die Makromolekulare Chemie*, vol. 190, No. 9, pp. 2255–2268 (1989).
M. Portugall et al., *Die Makromolekulare Chemie*, vol. 183, No. 10, pp. 2311–2321 (1982).

* cited by examiner

*Primary Examiner*—Shean C. Wu
(74) *Attorney, Agent, or Firm*—Millen, White, Zelano & Branigan, P.C.

(57) ABSTRACT

The invention relates to reactive liquid crystal compounds of Formula (I),

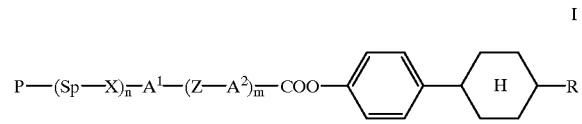

wherein P=polymerizable group, Sp=spacer, X and Z=linking group, n=1, m=0, or 1, $A^1$ and $A^2$=ring structure and R=unsubstituted or substituted alkyl group with the proviso that m=1 and/or R—P—Sp—X group. The composition comprising reactive liquid crystal compounds of formula (I), to linear or cross-linked (co) polymers obtainable by (co) polymerizing said reactive liquid crystals or compositions and to the use of said reactive liquid crystals or compositions for the preparation of linear or cross-linked polymers or polymer films for decorative pigments, cosmetics or security applications, active and passive optical elements, color filters, scattering displays, adhesives or synthetic resins with anisotropic mechanical properties.

13 Claims, 1 Drawing Sheet

REACTIVE LIQUID CRYSTAL COMPOUNDS

This is a continuation of application Ser. No. 09/117,787 filed Aug. 7, 1998, abandoned.

SUMMARY OF THE INVENTION

The invention relates to reactive liquid crystal compounds of formula I

I wherein

| | |
|---|---|
| P | is $CH_2=CW-COO-$, $WCH=CH-O-$, $WHC\overset{O}{\underset{}{-}}CH-$ or $CH_2=CH$-Phenyl-$(O)_k-$ with W being H, $CH_3$ or Cl and k being 0 or 1, |
| Sp | is a spacer group having 1 to 20 C atoms, |
| X | is $-O-$, $-S-$, $-CO-$, $-COO-$, $-OCO-$, $-S-CO-$, $-CO-S-$, $-OCOO-$ or a single bond, |
| n | is 0 or 1, |
| $A^1$ and $A^2$ | are each independently 1,4-phenylene in which, in addition, one or more CH groups may be replaced by N, 1,4-cyclohexenylene or 1,4-cyclohexylene in which, in addition, one or two non-adjacent $CH_2$ groups may be replaced by O and/or S, or naphthalene-2,6-diyl, it being possible for these rings to be substituted with halogen, cyano or nitro groups or with one or more alkyl, alkoxy or acyl groups with 1 to 7 C atoms wherein one or more H atoms may be substituted by F or Cl, |
| Z | is $-OCO-$, $-COO-$, $-CH_2CH_2-$, $-CH=CH-$, $-C\equiv C-$, $-CH_2O-$, $-OCH_2-$, or a single bond, |
| m | is 0 or 1, and |
| R | is an alkyl radical with up to 20 C atoms which may be unsubstituted, mono- or polysubstituted by halogen or CN, it being possible for one or more $CH_2$ groups to be replaced by $-O-$, $-S-$, $-NH-$, $N(CH_3)-$, $-CO-$, $-OCO-$, $-COO-$, $-S-CO-$, $-CO-S-$, $-O-COO-$ in such a manner that oxygen atoms are not directly linked to one another, or alternatively R is halogen, cyano or has independently one of the meanings given for $P-(Sp-X)_n-$. |

The invention furthermore relates to compositions comprising at least two reactive liquid crystal compounds at least one of which is a compound of formula I as specified above.

Another aspect of the invention are linear or crosslinked (co)polymers obtainable by (co)polymerizing at least one reactive liquid crystal compound of formula I or a composition as described above.

Yet another aspect of the invention is the use of reactive liquid crystal compounds or compositions as described above for the preparation of linear or crosslinked polymers or polymer films for decorative pigments, cosmetics or security applications, active and passive optical elements, like e.g. optical polarizer or compensator films, colour filters, scattering displays, adhesives or synthetic resins with anisotropic mechanical properties.

DETAILED DESCRIPTION OF THE INVENTION

Reactive liquid crystal compounds can be polymerized in situ when being macroscopically oriented in their liquid crystalline state to give anisotropic linear or crosslinked polymers and polymer films with a uniform orientation of high quality. Such materials can be used for example as optical elements like broad band cholesteric polarizers (see EP 0,606,940) or polarization filters (EP 0,397,263).

The European Application EP 0,451,905 describes scattering displays with anisotropic gels made of crosslinked diacrylates with phenyldibenzoate as mesogenic core and a low-molecular liquid crystalline material.

Reactive liquid crystal compounds of various molecular structures have been described in prior art. The WO 93/22397, EP 0,405,713 and DE 195,04,224 for example disclose reactive compounds with mesogenic cores consisting of phenylene, bi- or terphenylene or naphthalene ring systems linked by ester or ethylene groups and with terminal acrylate or epoxy groups as polymerizable groups.

The reactive liquid crystal compounds described in prior art, however, often exhibit liquid crystalline phases only in a small temperature range or do not show mesophase behaviour at all. Furthermore, they often have rather high melting points, which is in particular disadvantageous for the preparation of highly oriented anisotropic polymers, since the polymerization has then to be carried out at high temperatures. Another drawback of the reactive liquid crystal compounds of in prior art are their disadvantageous values of the birefringence.

For some applications it is useful to have anisotropic polymer films with good adhesion on plastic substrates. However, when polymerizing mixtures containing high amounts of reactive liquid crystal compounds with two polymerizable groups as disclosed in prior art, one obtains polymer films with high brittleness and poor adhesion.

There is therefore existing a demand for reactive liquid crystals with one polymerizable group to flexibilize mixtures and promote adhesion of the resulting polymer films.

Furthermore, regarding the broad range of applications for reactive liquid crystal compounds it is desirable for the expert to have available further compounds of this type which are easy to synthesize and fulfill the various requirements as described above.

It was therefore an aim of the invention to provide new reactive liquid crystal compounds with advantageous properties thus extending the pool of reactive liquid crystal compounds available to the expert. Other aims of the present invention are immediately evident to the person skilled in the art from the following detailed description.

The terms reactive mesogenic compound, reactive liquid crystal compound or reactive liquid crystalline compound as used in the foregoing and the following comprise compounds with a rodlike or boardlike mesogenic group. These compounds do not necessarily have to exhibit mesophase behaviour by themselves. It is also possible that they can show mesophase behaviour only in mixtures with other compounds or when the pure compounds or the mixtures are polymerized.

The object of the present invention are reactive liquid crystal compounds of formula I

I wherein

Another object of the present invention are compositions comprising at least two reactive liquid crystal compounds at least one of which is a compound of formula I.

Preferred embodiments of the invention are those wherein the reactive liquid crystalline compounds are compounds of formula I, wherein
n is 1,
m is 0 and $A^1$ is 1,4-phenylene,
Sp is alkylene with 1 to 15 C atoms,
R is halogen, cyano or an optionally fluorinated achiral or chiral alkyl or alkoxy group with 1 to 15 C atoms.

In another preferred embodiment of the invention the reactive liquid crystalline compounds are selected according to formula I, wherein R has one of the meanings of P—$(Sp-X)_n$— given above.

In a further preferred embodiment the composition comprising reactive liquid crystalline compounds as described above is characterized in that it comprises at least one compound having two or more polymerizable terminal groups.

In a further preferred embodiment said composition is characterized in that it comprises at least one compound having a polymerizable terminal group and a chiral terminal group.

Another aspect of the invention are linear or crosslinked (co)polymers obtainable by (co)polymerizing at least one reactive liquid crystal compound of formula I or a composition as described above.

Yet another aspect of the invention is the use of reactive liquid crystal compounds or compositions as described above for the preparation of linear or crosslinked polymers or polymer films for decorative pigments, cosmetics or security applications, active and passive optical elements, like e.g. optical polarizer or compensator films, colour filters, anisotropic gels, scattering displays, adhesives or synthetic resins with anisotropic mechanical properties.

Formula I covers the tricyclic and tetracyclic compounds of the sub-formulae I 1 and I 2:

| | |
|---|---|
| P-(Sp-X)ₙ-A¹-MG-R | I 1 |
| P-(Sp-X)ₙ-A¹-Z-A²-MG-R | I 2 | wherein MG denotes

Of the compounds of formula I 1 and I 2 especially preferred are those in which n is 1, R is alkyl or has the meaning given for P—Sp—X— and Z is —COO—, —OCO— or a single bond.

Of the mesogenic compounds which contain a heterocyclic group, those containing a pyridine-2,5-diyl group, pyrimidine-2,5-diyl group or 1,3-dioxane-2,5-diyl group are particularly preferred.

A smaller group of particularly preferred mesogenic compounds of the formulae I 1 and I 2 is listed below. For reasons of simplicity, PheS is 1,4-phenylene, which is substituted in 2- and/or 3-position with halogen, cyano or nitro groups or an alkyl, alkyloxy or acyloxy group having 1 to 7 C atoms wherein one or more H atoms may be substituted by F or Cl. Furthermore, Pyd is pyridine-2,5-diyl, Pyr is pyrimidine-2,5-diyl, Cyc is 1,4-cyclohexene, Dio is trans-1,3-dioxane-2,5-diyl and Dit is trans-1,3-dithiane-2,5-diyl. The notations Pyd, Pyr and Dio in each case include the two possible positional isomers.

Particularly preferred mesogenic compounds of the sub-formula I 1 are those of the sub-formulae I 1-1 to I 1-7:

| | |
|---|---|
| P-Sp-X-Phe-MG-R | I 1-1 |
| P-Sp-X-PheS-MG-R | I 1-2 |
| P-Sp-X-Cyc-MG-R | I 1-3 |
| P-Sp-X-Pyd-MG-R | I 1-4 |
| P-Sp-X-Pyr-MG-R | I 1-5 |
| P-Sp-X-Dio-MG-R | I 1-6 |
| P-Sp-X-Dit-MG-R | I 1-7 |

The compounds of formula I 1-1 to I 1-3 are preferred. In particular preferred are the compounds of formula I 1-1 and I 1-2.

Particularly preferred mesogenic compounds of the sub-formula I 2 are those of the sub-formulae I 2-1 to I 2-21:

| | |
|---|---|
| P-Sp-X-Phe-Z-Phe-MG-R | I 2-1 |
| P-Sp-X-Phe-Z-PheS-MG-R | I 2-2 |
| P-SP-X-PheS-Z-PheS-MG-R | I 2-3 |
| P-Sp-X-Phe-Z-Cyc-MG-R | I 2-4 |
| P-Sp-X-Cyc-Z-Phe-MG-R | I 2-5 |
| P-Sp-X-Cyc-Z-PheS-MG-R | I 2-6 |
| P-Sp-X-Cyc-Z-Cyc-MG-R | I 2-7 |
| P-Sp-X-Phe-Z-Pyd-MG-R | I 2-8 |
| P-Sp-X-Phe-Z-Pyr-MG-R | I 2-9 |
| P-Sp-X-Pyd-Z-Phe-MG-R | I 2-10 |
| P-Sp-X-Pyr-Z-Phe-MG-R | I 2-11 |
| P-Sp-X-Pyd-Z-PheS-MG-R | I 2-12 |
| P-Sp-X-Pyr-Z-PheS-MG-R | I 2-13 |
| P-Sp-X-Phe-Z-Dio-MG-R | I 2-14 |
| P-Sp-X-Dio-Z-Phe-MG-R | I 2-15 |
| P-Sp-X-Dio-Z-PheS-MG-R | I 2-16 |
| P-Sp-X-Phe-Z-Dit-MG-R | I 2-17 |
| P-Sp-X-Dit-Z-Phe-MG-R | I 2-18 |

-continued

| | |
|---|---|
| P-Sp-X-Dit-Z-PheS-MG-R | I 2-19 |
| P-Sp-X-Dio-Z-Dit-MG-R | I 2-20 |
| P-Sp-X-Dit-Z-Dio-MG-R | I 2-21 |

Of these compounds, those of formula I 2-1 to I 2-13 are preferred. Especially preferred are the compounds of formula I 2-1 to I 2-7, in particular those of formula I 2-1, I 2-2, I 2-4 and I 2-5.

Of the preferred compounds of formulae I 2-1 to I 2-21 in particular preferred are those in which Z is an ester group (—COO— or —OCO—), —CH₂—CH₂— or a single bond.

Of the preferred compounds containing a substituted 1,4-phenylene group very particularly preferred are those substituted by F, Cl or methyl.

In the mesogenic compounds of the formula I, R is preferably an alkyl radical which is unsubstituted or substituted by at least one halogen atom, it being possible for one or two non-adjacent CH₂ groups of these radicals to be replaced by —O—, —S—, O—CO—, —CO—O— or —O—CO—O— groups. Halogen is preferably F or Cl.

If R is an alkyl or alkoxy radical, i.e. where the terminal CH₂ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

Oxaalkyl, i.e. where one CH₂ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

R may be an achiral or a chiral group. In case of a chiral group it is preferably selected according to formula II:

II wherein

X has the meaning given above,

Q¹ is an alkyl or alkoxy group with 1 to 7 C atoms or a single bond,

Q² is an alkyl or alkoxy group with 1 to 8 C atoms which may be unsubstituted, mono- or polysubstituted by halogen or CN, it being also possible for one or more non-adjacent CH₂ groups to be replaced, in each case independently from one another, by —O—, —S—, —NH—, —N(CH₃)—, —CO—, —COO—, —OCO—, —OCO—O—, —S—CO— or —CO—S— in such a manner that oxygen atoms are not linked directly to one another, or has the meaning given for P—Sp—, Q³ is halogen, a cyano group or an alkyl or alkoxy group with 1 to 4 C atoms different from Q².

Preferred chiral groups are 2-butyl (=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, for example.

In addition, mesogenic compounds of the formula I containing an achiral branched group R may occasionally be of importance as comonomers, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl propoxy and 3-methyl butoxy.

In another preferred embodiment the chiral group is selected from the following groups:

a cholesteryl group, an ethylenglycol derivative wherein $R^1$ is an alkyl radical with 1 to 12 C atoms, a terpenoid radical like, for example, menthol or a group based on citronellol In the compounds of formula I P is $CH_2$=CW—COO, WCH=CH—O— or $CH_2$=CH—Phenyl—(O)$_k$— with W being H, $CH_3$ or Cl and k being 0 or 1.

Preferably P is a vinylether or propenylether group, an acrylate or methacrylate group or an epoxy group. Especially preferred are the following meanings of P:

| | |
|---|---|
| $CH_2$=CH—COO— | acrylate |
| $CH_2$=C($CH_3$)—COO— | methacrylate |
|  | epoxy group |

As for the spacer group Sp all groups can be used that are known for this purpose to the skilled in the art. The spacer group is preferably linked to the polymerizable group P by an ester or ether group or a single bond. It is preferably a linear or branched alkylene group having 1 to 20 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)—, —CH(CN)—, —CH=CH— or —C≡C—.

Typical spacer groups are for example —($CH_2$)$_o$—, —($CH_2CH_2$O)$_r$—$CH_2CH_2$—, —$CH_2CH_2$—S—$CH_2CH_2$— or —$CH_2CH_2$—NH—$CH_2CH_2$—, with o being an integer from 2 to 12 and r being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyl-iminoethylene and 1-methylalkylene, for example.

In particular preferred are compounds of formula I wherein n is 1.

In another preferred embodiment, the polymers are copolymers obtained by copolymerizing mixtures comprising compounds of formula I wherein n is 0 and compounds of formula I wherein n is 1.

In the event that R or $Q^2$ is a group of formula P—Sp—X— or P—Sp— respectively, the spacer groups on each side of the mesogenic core may be identical or different.

Anisotropic polymers can be prepared by solution polymerization or by in-situ polymerization. Solution polymerization can be carried out for example in a solvent like dichloromethane, tetrahydrofuran or toluene using AIBN as an initiator and heating for 24 hours at 30 to 60° C. However, in order to obtain polymers with macroscopic uniform orientation, the polymers prepared by solution polymerization have to be aligned afterwards by special means like electric or magnetic fields and high temperatures.

On the other hand, mesogenic monomers like the inventive compounds can easily be aligned by conventional techniques and the alignment can subsequently be frozen in by in-situ polymerization. A detailed description of this method can be found in D. J. Broer et al., Makromol.Chem. 190, 2255ff. and 3202ff. (1989).

The reactive liquid crystal compounds and compositions according to this invention are preferably polymerized in situ as described in the foregoing and the following.

Polymerization of reactive mesogenic compounds or compositions comprising compounds with only one polymerizable functional group leads to linear polymers or copolymers, whereas in the presence of compounds with more than one polymerizable functional group crosslinked polymers are obtained.

In particular crosslinked polymers show very high thermal stability of the optical and mechanical properties, depending on the degree of crosslinking, when compared to linear polymers.

Linear or crosslinked polymers or copolymers are obtained for example by exposure of the inventive reactive liquid crystal compounds or compositions to actinic radiation in the presence of an initiator having an absorption maximum adjusted to the wavelength of said radiation.

For example, one can use UV light and a photoinitiator that decomposes under UV irradiation to produce free radicals that start the polymerization reaction. In another preferred embodiment a cationic photoinitiator is used that photocures with cations instead of free radicals. The polymerization may also be started by an initiator that decomposes when heated above a certain temperature.

As a photoinitiator for example the commercially available Irgacure 651 (from Ciba Geigy AG) can be used.

Polymerization of reactive liquid crystal compounds or compositions comprising compounds with only one polymerizable functional group leads to linear polymers or copolymers, whereas in the presence of compounds with more than one polymerizable functional group crosslinked polymers are obtained.

In addition to light- or temperature-sensitive initiators said compositions may also comprise one or more other suitable components such as, for example, catalysts, stabilizers, co-reacting monomers or surface-active compounds.

It is alternatively possible to add, for example, a quantity of up to 20% by weight of a nonpolymerizable liquid-crystalline material to adapt the optical properties of the polymer.

It is also possible to add up to 20% of a non mesogenic compound with two or more polymerizable functional groups to increase crosslinking of the polymers. Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

To prepare anisotropic polymer films with uniform orientation the inventive reactive liquid crystal compounds or compositions, for example, are coated onto a substrate, aligned and cured by irradiating as described above. Alignment and curing are hereby carried out in the mesophase of the reactive liquid crystal compounds.

As a substrate for example a glass plate or a plastic film can be used. To achieve uniform alignment, the film can be sheared for example by means of a doctor's blade. In another preferred embodiment, a second substrate is put on top of the coated material. In this case, the shearing caused by putting together the two substrates is sufficient to give good alignment.

In some embodiments it is of advantage to apply a second substrate in order to exclude oxygen that may inhibit the polymerization. Alternatively the curing can be carried out under a nitrogen atmosphere. In the latter case shearing of the mesogenic material prior to polymerization is necessary to cause sufficient alignment of the mesophase. When using a cationic photoinitiator oxygen exclusion is not needed, but water should be excluded.

The compounds of the present invention can be used in mixtures with other reactive liquid crystal compounds to give mixtures with low melting points. This is of importance especially when anisotropic polymer films are prepared. To obtain highly oriented films the polymerization has to be carried out in the liquid crystal phase of the reactive liquid crystal mixture. Thus by using the compounds of this invention the polymerization temperature can be lowered significantly and the polymerization process is made easier.

Another object of the invention is to provide compounds for polymer films with good adhesion to plastic substrates. Crosslinked anisotropic polymers made from mixtures containing high amounts of reactive liquid crystal compounds with two functional polymerizable groups exhibit a good heat resistance. On the other hand, with increasing amount of the difunctional reactive liquid crystal compounds the brittleness of the polymer is increasing and the adhesion to substrates is decreasing.

Thus a special preferred embodiment of the invention are compounds of formula I, wherein R is an achiral alkyl or alkoxy group, used for the preparation of polymers in order to balance the heat resistance and the adhesion of the resulting polymer films.

Another preferred embodiment of the invention is a mixture comprising at least two reactive liquid crystal compounds at least one of which is a compound as described in the previous paragraph, characterized in that the mixture contains not more than 20% of a compound having two or more polymerizable groups.

The reactive liquid crystal compounds according to formula I can be prepared by methods which are known per se and which are described, for example, in standard works of organic chemistry such as, for example, Houben-Weyl, Methoden der organischen Chemie, Thieme-Verlag, Stuttgart. Some specific methods of preparation can be taken from the examples.

Without further elaboration, it is believed that one skilled in the art can, using the preceding description, utilize the present invention to ist fullest extent. The following examples are, therefore, to be construed as merely illustrative and not limitative of the remainder of the disclosure in any way whatsoever.

The entire disclosure of all applications, patents and publications, cited above and below, are hereby incorporated by reference.

In the foregoing and in the following examples, all temperatures are set forth uncorrected in degrees Celsius and unless otherwise indicated, all parts and percentages are by weight. The following abbreviations are used to illustrate the liquid crystalline phase behaviour of the compounds:

C=crystalline; N=nematic; S=smectic; $S_A$=smectic A; Ch=cholesteric; I=isotropic. The numbers between these symbols indicate the phase transition temperatures in degree Celsius.

The following abbreviations are used:

| | |
|---|---|
| DMF | dimethylformamide |
| DCM | dichloromethane |
| DCCI | dicyclohexylcarbodiimide |

EXAMPLES

Example 1

The reactive liquid crystal compounds of formula (3)

are prepared according to the following reaction scheme:

The synthesis of the benzoic acid (1) is disclosed in D. J. Broer et al., Makromol.Chem. 190, 2255 (1989). The phenol (2) can be prepared in an analoguous manner to the compounds de scribed in DE 2,636,684.

The compounds (1) exhibit the following mesophase behaviour:

| No. | x | y | phase behaviour |
|---|---|---|---|
| 3a | 6 | 3 | C 66 N 154 I |
| 3b | 6 | 4 | C 74 N 186 I |
| 3c | 6 | 5 | C 74 S 102 N 151 I |
| 3d | 3 | 5 | C 90 N 163 I |
| 3e | 3 | 7 | C 68 N 164 I |
| 3f | 3 | 3 | C 88 N 171 I |
| 3g | 3 | 4 | C 98 N 160 I |

Example 2

A mixture is formulated consisting of

| | |
|---|---|
| compound (3a) | 60% |
| compound (3f) | 40% |

The mixture exhibits the mesophase behaviour C 43 N 160 I with a significantly low melting point.

Example 3

A mixture is formulated consisting of

| | |
|---|---|
| compound (3a) | 27% |
| compound (3f) | 18% |
| compound (4) | 55% |

(4)

The preparation of compound (4) is described in DE 195,04,224. The mixture is melting below room temperature and exhibits the mesophase behaviour $S_A$ 24.4 Ch 67 I. The mixture is cured between two glass slides by exposure to UV light at a temperature of 35° C. A cholesteric copolymer is formed with a glass transition temperature Tg of 1.8° C. and a reflection wavelength of 549 nm.

Example 4

The following mixtures are formulated:

|  | 4A | 4B | 4C | 4D |
|---|---|---|---|---|
| compound (3a) | 25.2% | 23.4% | 20.4% | 17.4% |
| compound (3f) | 16.8% | 15.6% | 13.6% | 11.6% |
| compound (4) | 55% | 55% | 55% | 55% |
| compound (5) | 2% | 5% | 10% | 15% |
| Irgacure 651 | 1% | 1% | 1% | 1% |

(5)

The direactive compound (5) can be prepared as described in WO 93/22397 and serves as crosslinking agent to increase Tg and thereby the brittleness of the polymer. Irgacure 651 is a commercially available photoinitiator from Ciba Geigy AG, Basel, Switzerland.

The mixtures exhibit the following mesophase behaviour:

| 4A | $S_A$ 22 Ch 66.1 I |
| 4B | $S_A$ 19 Ch 64.8 I |
| 4C | $S_A$ 14 Ch 62.9 I |
| 4D | $S_A$ 9 Ch 60.0 I |

The mixtures are put between two glass slides coated with a layer of rubbed polyimide and cured by exposure to UV light in the cholesteric phase at temperatures of 35 to 40° C. The resulting polymer films exhibit the following values for Tg and the reflection wavelength λ while showing different quality of adhesion when put on a plastic substrate:

|  | 4A | 4B | 4C | 4D |
|---|---|---|---|---|
| Tg (° C.) | 4 | 6 | 10 | 12 |
| λ (nm) | 548 | 540 | 534 | 524 |
| content of (5) | 2% | 5% | 10% | 15% |

When going from 4D to 4A, the adhesion of the films is improving with decreasing amount of direactive compound (5). In the same direction the polymer films become more flexible, as is indicated by the decrease of Tg.

Example 5

The reactive liquid crystal compounds of formula (6)

are prepared by the following synthetic route:

(6)

The following compounds were prepared and their mesophase behaviour was investigated:

| No. | n | R | phase behaviour |
|---|---|---|---|
| 6a | 9 | $C_3H_7$ | C 74 N 166 I |
| 6b | 9 | $C_4H_9$ | C 87 N 161 I |
| 6c | 9 | $C_5H_{11}$ | C 71 $S_A$ 102 N 165 I |

Example 6

The reactive liquid crystal compounds of formula (7)

are prepared by the following synthetic route:

The compound with n=8 and R=$C_4H_9$ exhibits the mesophase behaviour C 68 N 167 I.

Example 7

The following mixture was formulated

| | |
|---|---:|
| compound (3a) | 40.1% |
| compound (3f) | 29.2% |
| compound (5) | 22.6% |
| compound (8) | 3.4% |
| Irgacure 907 | 4.0% |

(8)

Irgacure is a photoinitiator available from Ciba Geigy AG.

The direactive compound (8) can be prepared as described in WO 93/22397.

The mixture exhibits the mesophase behaviour C 40 N 138 I but supercools to room temperature without crystallization. The optical anisotropy Δn is 0.157, measured at 20° C. with light of a wavelength of 600 nm.

Figure 1:
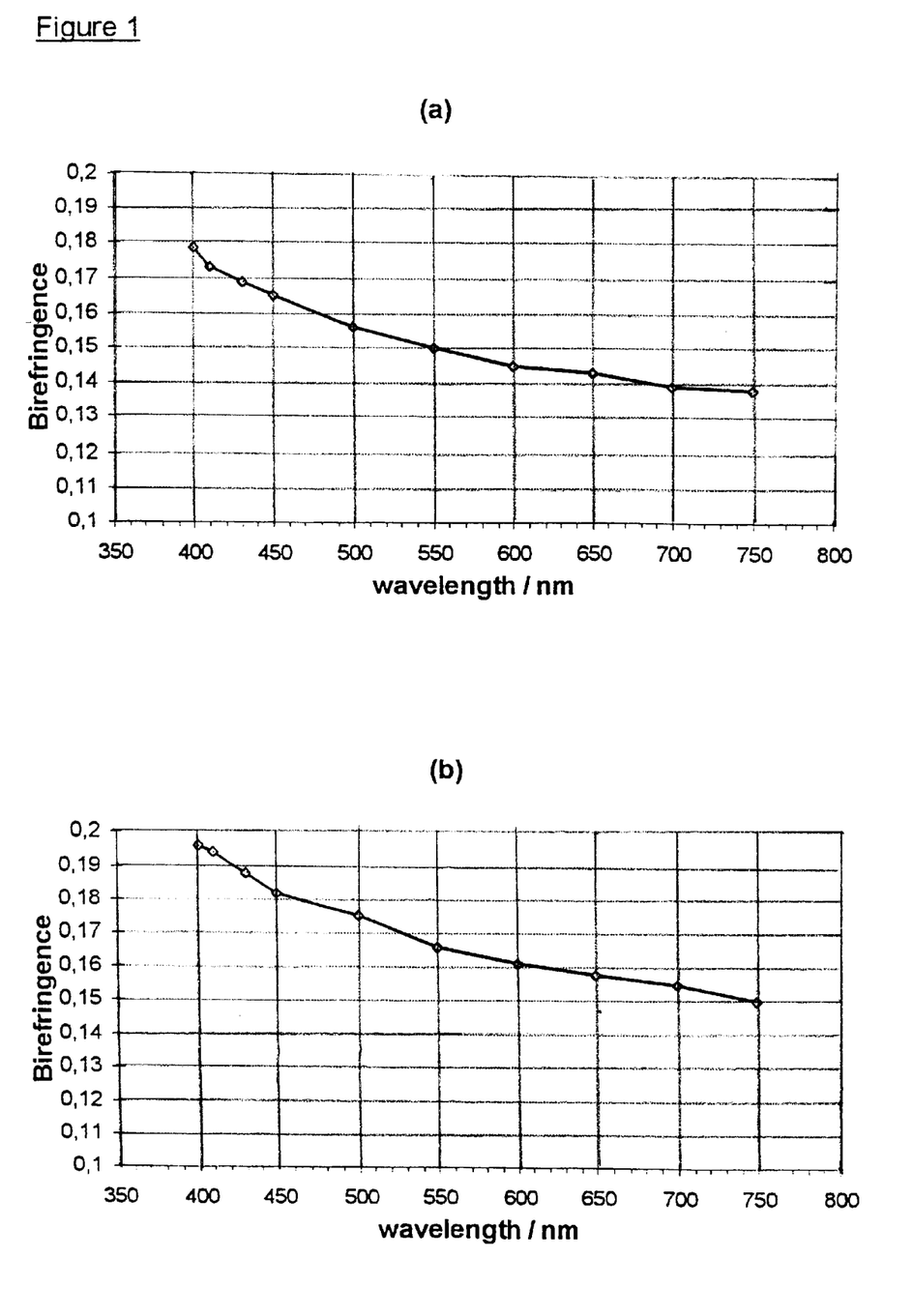
FIG. 1 shows the birefringence versus wavelength of a cured (1a) and an uncured (1b) composition according to the present invention.

The mixture is homogeneously aligned between two glass slides and cured by exposure to UV light at 20° C. to give a polymer film with a birefringence of 0.144 (600 nm, 20° C.). The variation of the birefringence versus wavelength is shown in FIG. 1a for the cured and in FIG. 1b for the uncured mixture.

Example 8

The following mixture was formulated

| | |
|---|---:|
| compound (3a) | 65% |
| compound (5) | 5% |
| compound (9) | 30% |

(9)

The preparation of compound (9) is described for example in M. Portugall et al., Makromol. Chem. 183, 2311 (1982).

The mixture has the mesophase behaviour C 30 $S_A$ 55 N 114 I.

Example 9

The following mixture was formulated

| | |
|---|---:|
| compound (3a) | 35% |
| compound (3c) | 30% |
| compound (5) | 5% |
| compound (9) | 30% |

The mixture has the mesophase behaviour C 30 $S_A$ 62 N 107 I.

What is claimed is:

1. A reactive liquid crystal compound of formula I

I wherein

P is $CH_2$=CW—COO—, WCH=CH—O—, or $CH_2$ = CH-Phenyl-$(O)_n$-with W being H, $CH_3$ or Cl, Sp is a spacer group having 1 to 20 C atoms, X is —O—, —S—, —CO—, —COO—, —OCO—, —O—COO—, —S—CO—, —CO—S— or a single bond, n is 1, $A^1$ and $A^2$ are each independently 1,4-phenylene in which, in addition, one or more CH groups may be replaced by N, 1,4-cyclohexenylene or 1,4-cyclohexylene in which, in addition, one or two non-adjacent $CH_2$ groups may be replaced by O and/or S, or naphthalene 2,6-diyl these rings optionally being substituted with halogen, cyano or nitro groups or with one or more alkyl, alkoxy or acyl groups with 1 to 7 C atoms wherein one or more H atoms may be substituted by F or Cl, Z is —OCO—, —COO—, —$CH_2CH_2$—, —CH=CH—, —C≡C—, —$CH_2$O—, —OCH—, or a single bond, m is 0 or 1, R is an alkyl radical with up to 20 C atoms which may be unsubstituted, mono- or polysubstituted by halogen or CN, one or more $CH_2$ groups optionally being replaced by —O—, —S—, —NH—, N(CH$_3$)—, —CO—, —OCO—, —COO—, —S—CO—, —CO—S—, —O—COO—, in such a manner that oxygen atoms are not directly linked to one another, or alternatively R is halogen, cyano or is P—(Sp—X)$_{n'}$—, and n' is 0 or 1, with the proviso that m is 1 and/or R is P—(Sp—X)$_{n'}$.

2. A reactive liquid crystalline compound of claim 1, wherein m is 0 and A$^1$ is 1,4-phenylene substituted by halogen, cyano or nitro groups, or by one or more alkyl, alkoxy or acyl groups with 1 to 7 C atoms wherein one or more H atoms may be substituted by F or Cl.

3. A reactive liquid crystalline compound of claim 1, wherein n is 1 and Sp is alkylene with 1 to 15 C atoms.

4. A reactive liquid crystalline compound of claim 1, wherein R is halogen, cyano or an optionally fluorinated achiral or chiral alkyl or alkoxy group with 1 to 15 C atoms.

5. A composition comprising at least two reactive liquid crystalline compounds, at least one of which is a compound of formula I according to claim 1.

6. A composition according to claim 5, comprising at least one compound having two polymerisable terminal groups.

7. A composition according to claim 5, comprising at least one compound having a polymerisable terminal group and a chiral terminal group.

8. A linear or crosslinked (co) polymer obtainable by (co) polymerizing at least one monomer of claim 1.

9. A decorative pigment, cosmetic, security application, active or passive optical element, an optical polarizer or compensator film, a color filter, a scattering display, an adhesive or synthetic resin with anisotropic mechanical properties, containing an anisotropic polymer, wherein the polymer is one of claim 8.

10. A process for the preparation of a polymer having anisotropic properties, comprising polymerizing a reactive liquid crystal compound of claim 1.

11. A compound of claim 1, wherein m is 1 and A$^1$ and A$^2$ are unsubstituted phenylene.

12. A compound of claim 1, wherein m is 1 and at least one of A$^1$ or A$^2$ are phenylene substituted by halogen, cyano or nitro groups, or by one or more alkyl, alkoxy or acyl groups with 1 to 7 C atoms wherein one or more H atoms may be substituted by F or Cl.

13. A reactive liquid crystalline compound of claim 1, wherein R is P—(Sp—X)$_{n'}$.

* * * * *